United States Patent [19]

Nishimura et al.

[11] 4,348,905

[45] Sep. 14, 1982

[54] VIBRATION SENSOR FOR AN AUTOMOTIVE VEHICLE

[75] Inventors: Toshifumi Nishimura, Yokosuka; Kunihiko Sugihara, Takasho, both of Japan

[73] Assignee: Nissan Motor Company, Limited, Yokohama, Japan

[21] Appl. No.: 166,947

[22] Filed: Jul. 8, 1980

[30] Foreign Application Priority Data

Jul. 13, 1979 [JP] Japan .............................. 54-96577[U]

[51] Int. Cl.³ ............................................. G01L 23/22
[52] U.S. Cl. ....................................... 73/654; 310/329
[58] Field of Search ..................... 73/35, 654; 310/328, 310/329, 330, 332, 340, 348, 354, 356; 29/25.35

[56] References Cited

U.S. PATENT DOCUMENTS

| | | | |
|---|---|---|---|
| 2,619,605 | 11/1952 | Lancor | 73/35 |
| 3,113,223 | 12/1963 | Smith et al. | 73/517 R X |
| 3,387,149 | 6/1968 | Young | 310/330 |
| 4,103,264 | 7/1978 | Howatt et al. | 310/340 |

FOREIGN PATENT DOCUMENTS

| | | |
|---|---|---|
| 860767 | of 0000 | United Kingdom . |
| 868148 | of 0000 | United Kingdom . |
| 878935 | of 0000 | United Kingdom . |
| 919157 | of 0000 | United Kingdom . |
| 1349354 | of 0000 | United Kingdom . |
| 1465970 | of 0000 | United Kingdom . |
| 2002955 | of 0000 | United Kingdom . |
| 2011165 | of 0000 | United Kingdom . |

*Primary Examiner*—James J. Gill
*Attorney, Agent, or Firm*—Thompson, Birch, Gauthier & Samuels

[57] ABSTRACT

A vibration sensor for an automotive vehicle including a piezoelectric vibrator of cantilever type for detecting mechanical vibrations, such as knocking, from an engine body. The vibration sensor prevents the vibrator from being deformed by thermal stress even if temperature near the sensor rises sharply, so that a stable resonant frequency will be maintained when detecting the vibration of an engine body.

4 Claims, 8 Drawing Figures

VIBRATION SENSOR FOR AN AUTOMOTIVE VEHICLE

BACKGROUND OF THE INVENTION

1. Field of the Invention

The present invention relates generally to a vibration sensor for an automotive vehicle which can detect mechanical vibrations generated from an internal combustion engine, such as knocking, and more specifically to a vibration sensor for an automotive vehicle having a piezoelectric vibration element therein mounted in cantilever fashion.

2. Description of the Prior Art

Generally, if strong engine knocking continues for a long time while an internal combustion engine is in operation, the knocking will adversely affect the engine's durability and performance. However, it has also been known that the best engine operating conditions with respect to engine torque characteristics and fuel consumption rate can be obtained when the engine rotates with a weak knocking at a relatively slow engine speed.

Heretofore, various systems have been proposed which can detect engine knocking conditions and regulate the engine spark timing so as to maintain a weak knocking state at all times for improvement in engine torque characteristics and fuel consumption rate.

Engine spark timing control systems of this sort have already been disclosed by U.S. Pat. No. 4,002,155 and No. 4,012,942.

In the systems mentioned above, a vibration sensor is indispensable in order to detect the knocking conditions of an internal combustion engine, that is, to detect the engine vibration accompanied with knocking.

Conventionally, a round-shape piezoelectric vibration element has been used for this vibration sensor. Since a conventional round-shape piezoelectric vibration is fixed to the housing at its periphery, the vibration is susceptible to thermal deformation whenever the temperature changes sharply, thereby resulting in a change in resonant frequency of the vibrator.

Therefore, there has been a need for a vibration sensor for an automotive vehicle which is stable enough despite any abrupt temperature change without changing the resonant frequency of the vibrator.

BRIEF SUMMARY OF THE INVENTION

With these problems in mind, therefore, it is the primary object of the present invention to provide a vibration sensor for an automotive vehicle which is mounted in cantilever fashion in order to prevent thermal deformation.

To achieve the above-mentioned object, the vibrator sensor of the present invention comprises a housing with a hollow cavity, a piezoelectric element mounted therein in cantilever fashion, and two lead wires, one end of the vibrator being fixed to the housing, the other end thereof being free to vibrate within the hollow cavity. The two lead wires attached to the vibrator to conduct a piezoelectric signal are fixed to the vibrator by a bonding material or in a one-step plastic molding process.

BRIEF DESCRIPTION OF THE DRAWINGS

The features and advantages of the vibration sensor according to the present invention will be more clearly appreciated from the following description taken in conjunction with the accompanying drawings in which like reference numerals designate corresponding elements, and in which.

DETAILED DESCRIPTION OF THE PREFERRED EMBODIMENTS

Figure 1:
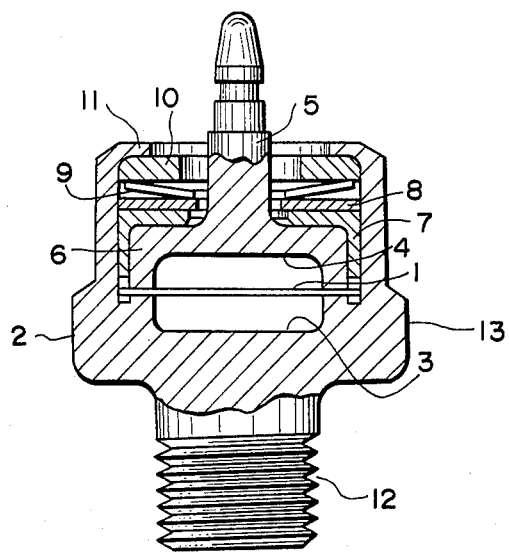
FIG. 1 is a vertical sectional view of a prior art vibration sensor.

To facilitate understanding of the present invention, a brief reference will be made to a conventional vibration sensor for an automotive vehicle. Referring to FIG. 1, the numeral 1 denotes a thin, round diaphragm vibrator made of a piezoelectric element, both surfaces of which are coated by, for example, silver to form electrode surfaces.

The vibrator 1 is housed in a housing 2 having a concave portion 3, and is clamped by an electrode 5 having a flange 6 to form another concave portion 4. The vibrator 1 is excited by the housing 2 to produce diaphragm vibration.

One of the electrode surfaces of the vibrator 1 is connected to the conductive housing 2; the other is connected to the conductive electrode 5.

To fix the diaphragm vibrator 1 under a constant clamping force, a dish-shaped spring 9 is placed between a spring sheet 8 and a retainer 10. The numeral 7 denotes an insulator. The retainer 10 is fixed by bending inward the cylindrical housing end to form a flange portion 11.

Since the diaphragm vibrator 1 is clamped by the elastic force of the dish-shaped spring 9 under almost constant pressure, it is possible to prevent the resonant frequency of the vibrator 1 from being varied according to the vibrator fixing pressure. In addition, the diameter of the concave portion 3 of the housing 2 is designed to be equal to that of the concave portion 4, so that the vibrator supporting internal diameters of both parts coincide. In this case, the support internal diameter is determined so that a resonant frequency of the vibrator 1 may range over the usual engine knocking frequencies between 5 and 9 KHZ.

The vibration sensor thus constructed is fixed onto an engine body with an anchor bolt 12 integrally formed with the housing 2. In addition, the base portion 13 of the housing 2 is hexagonal in shape for easy grasping with conventional mechanics' tools.

When the vibrator 1 begins to vibrate up and down with its periphery as the fulcrum in tune with the vibration of an engine body, a difference in potential is generated between the two electrode surfaces of the piezoelectric element in accordance with the deformation rate. Since one electrode surface is grounded through the housing 2, it is possible to transduce a mechanical vibration of the vibrator 1 (of the piezoelectric element) into a voltage signal between the electrode 5 and the engine body ground. Further, since the vibrator 1 is so designed to resonate within the knocking frequency range of an engine, it is possible to detect the vibration due to knocking efficiently and accurately.

However, the vibrator of this type has the following shortcomings:

Since the vibrator is fixedly supported at its periphery, when the temperature within the vibrator changes sharply, internal stress of tension or contraction within the vibrator results in deformation of the vibrator. That is to say, the vibrator is, therefore, susceptible to changes in resonant frequency.

Figure 2:
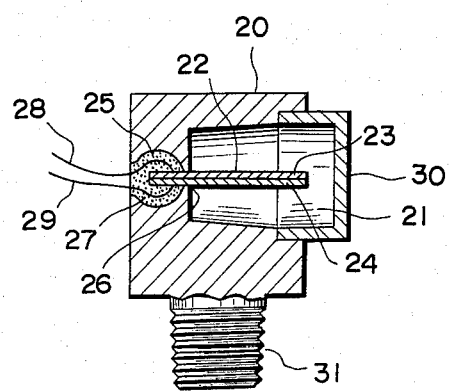
FIG. 2 is a vertical sectional view showing an embodiment of the vibration sensor according to the present invention.

In view of the above description, reference is now made to FIGS. 2, 3, 4, 5 and 6, and more specifically to FIG. 2, wherein a preferred embodiment of the vibrator sensor of the present invention is illustrated.

Figure 3:
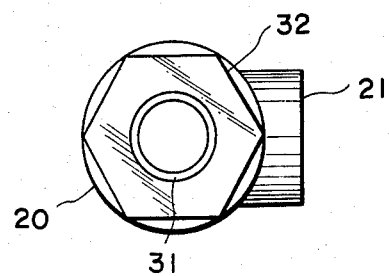
FIG. 3 is a bottom view of the embodiment shown in FIG. 2.

In FIGS. 2 and 3, the numeral 20 denotes a housing having a hollow cavity 21 in which a vibrator 22 is mounted and having an anchor bolt 31 integrally formed therewith.

The vibrator 22 comprises two rectangular, thin piezoelectric elements 23 and 24 adhered to each other with a conductive bonding material, and electrode surfaces coated on both the sides of the piezoelectric element. Commonly termed a Bimorph cell, the vibrator 22 of this type is constructed so that the electrode surfaces of the same polarity face each other so that piezoelectricity of each element will be doubled when the two elements are bent in the same direction.

One end of the vibrator 22 is initially inserted into a second cavity 25 after being passed through an elongate opening slit 26. Lead wires 28 and 29 are connected to the electrode surfaces of the piezoelectric elements 23 and 24 by, for example, soldering. The lead wires 28 and 29 extend from the second cavity 25, as shown. The vibrator 22 is next fixed within the second cavity 25 with a bonding material 27 so that the effective length thereof is determined by the distance from the end surface of the slit 26 to the free end of the vibrator.

In order to make the hollow cavity 21 within the housing 20 air-tight, protective cover 30 is fitted to the housing 20 from the outside.

In addition, the numeral 32 in FIG. 3 denotes a hexagonal portion of the housing, which is used when mounting the vibration sensor to an engine body.

In the vibration sensor constructed above, the vibrator 22 is excited with the supported end as the fulcrum whenever vibration is transmitted from the engine body to the vibrator housing 20. Whenever the vibrator is deformed, the piezoelectric elements 23 and 24 generate an electric signal to be transmitted through the lead wires 28 and 29.

In order to detect knocking vibration of an engine, it is necessary to equalize a vibrator resonant frequency to the knocking frequency. Accordingly, the vibrator 22 is first mounted so as to have a relatively low resonant frequency and is next adjusted into a desired length by cutting off the free end of the vibrator 22 so as to have a desired resonant frequency.

In this case, even if expanded or contracted due to temperature changes, the vibrator 22 mounted in such cantilever fashion is not subject to thermal stress. Therefore the vibrator characteristics are kept stable despite a temperature rise from the engine body.

In addition to the above, the positions where the lead wires 28 and 29 are soldered onto the vibrator electrode surfaces are fully covered by a bonding material, and therefore the lead wires are prevented from being peeled off from the surfaces even if the vibrator vibrates strongly.

Figure 4:
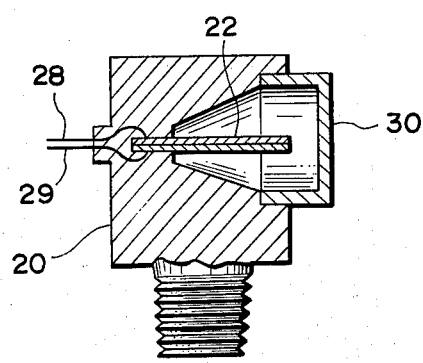
FIG. 4 is a vertical sectional view showing another embodiment of the vibration sensor according to the present invention.

FIG. 4 shows another embodiment of the present invention. In this embodiment, a housing 20 is integrally molded as one body from a plastic material and one end of the piezoelectric vibrator 22 and two lead wires 28 and 29 are all embedded together into the housing in a one-step process, without the use of any bonding material.

Figure 5:
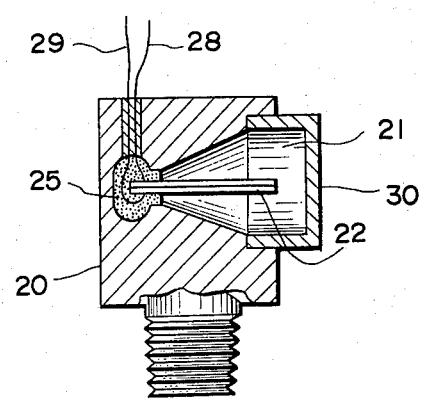
FIG. 5 is a vertical sectional view showing a third embodiment of the vibration sensor according to the present invention.

FIG. 5 shows the third embodiment of the present invention. In this embodiment, a housing 20 is formed with an additional passageway from the second cavity 25 and the lead wires are taken out therethrough. A vibrator 22 is fixed within the hollow cavity 21 by introducing a bonding material into the second cavity 25. In this embodiment, it is possible to regulate the effective length of the vibrator by adjusting the amount of bonding material.

Figure 6:
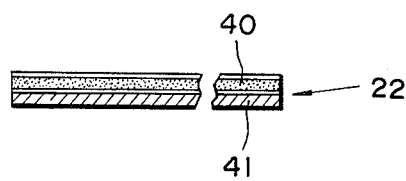
FIGS. 6 (A), (B) and (C) are vertical longitudinal sectional views showing piezoelectric vibration elements of various types.
Figure 6:
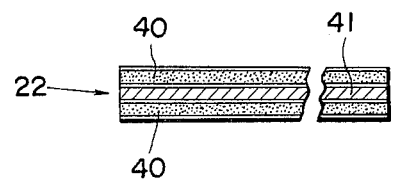
Figure 6:
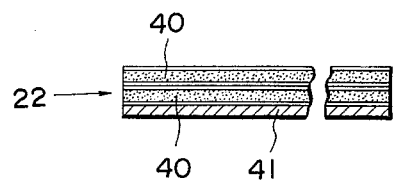

In the above description, only a vibrator 22 of the Bimorph cell type has been described in which two piezoelectric elements are bonded to each other; however, it is of course possible to use various types of vibrators, as depicted in FIGS. 6 (A) to 6 (C).

In FIG. 6 (A), a metal plate 41 is bonded by a conductive bonding material to one side of a dual electrode piezoelectric element 40; in FIG. 6 (B), the metal plate is bonded by a conductive bonding material between two piezoelectric elements 40; and in FIG. 6 (C), the metal plate is bonded to one side of two piezoelectric elements bonded to each other. In these cases, the metal plate 41 is used for reinforcing the vibrator element.

As described hereinabove, being mounted in cantilever fashion, the vibrator of the present invention is not subject to deformation due to thermal stress, and therefore is able to accurately detect knocking vibrations of an engine body where temperature changes frequently and sharply.

It will be understood by those skilled in the art that the foregoing description is in terms of preferred embodiments of the present invention wherein various changes and modifications may be made without departing from the spirit and scope of the invention, which is to be defined by the appended claims.

What is claimed is:

1. A vibration sensor for an automotive vehicle comprising:
    (a) a housing having a first cavity, a second cavity, and an opening in said housing between said cavities;
    (b) an elongated piezoelectric vibration element extending through said opening, the free end of said element being positioned within said first cavity to vibrate freely therein in cantilever fashion, the fixed end of said element being positioned within said second cavity and being fixed in position therein by a bonding material; and
    (c) means for conducting a piezoelectric signal in response to the vibration of said piezoelectric element, said means for conducting the signal being fixed in position within said second cavity by a bonding material.

2. A vibration sensor as set forth in claim 1, wherein said housing opening is larger than said vibration element, and said vibration element is fixed in position in said second cavity by a selected amount of bonding material, the amount of bonding material used determining the effective vibrating length of said vibration element.

3. A vibration sensor for an automotive vehicle as set forth in claims 1 or 2, further comprising a protection cover mounted on said housing to enclose said vibration element.

4. A vibration sensor for an automotive vehicle as set forth in claim 3, further comprising an anchor bolt to mount said housing to an engine body.

* * * * *